(12) United States Patent
Yoshimura et al.

(10) Patent No.: US 11,690,402 B2
(45) Date of Patent: Jul. 4, 2023

(54) CIRCUIT BOARD FOR NON-COMBUSTION TYPE FLAVOR INHALER AND NON-COMBUSTION TYPE FLAVOR INHALER

(71) Applicant: JAPAN TOBACCO INC., Tokyo (JP)

(72) Inventors: Tetsuya Yoshimura, Tokyo (JP); Masato Miyauchi, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 332 days.

(21) Appl. No.: 16/868,256

(22) Filed: May 6, 2020

(65) Prior Publication Data
US 2020/0260789 A1  Aug. 20, 2020

Related U.S. Application Data

(63) Continuation of application No. PCT/JP2017/040809, filed on Nov. 13, 2017.

(51) Int. Cl.
*A24F 40/46* (2020.01)
*A24B 15/167* (2020.01)
(Continued)

(52) U.S. Cl.
CPC ............ *A24F 40/46* (2020.01); *A24B 15/167* (2016.11); *A24F 40/50* (2020.01); *A24F 40/57* (2020.01); *H05K 1/0298* (2013.01); *H05K 1/0306* (2013.01); *H05K 1/0386* (2013.01); *H05K 1/092* (2013.01); *H05K 3/1283* (2013.01); *A24F 40/10* (2020.01); *A24F 40/20* (2020.01); *B82Y 30/00* (2013.01); *H05K 2201/017* (2013.01); *H05K 2201/0154* (2013.01); *H05K 2201/0284* (2013.01); *H05K 2201/0293* (2013.01)

(58) Field of Classification Search
CPC ......... H05K 1/092; H05K 1/09; A24F 40/50; A24F 40/57; A24F 40/46; A24B 15/167
USPC .......................................... 131/329
See application file for complete search history.

(56) References Cited

U.S. PATENT DOCUMENTS 5,447,753 A   9/1995  Noda et al.
2004/0200492 A1  10/2004  Brooks
(Continued)

FOREIGN PATENT DOCUMENTS

EP   2 316 286 A1   5/2011
JP   2003-3154 A    1/2003
(Continued)

OTHER PUBLICATIONS

Extended European Search Report for European Application No. 17931535.3, dated Jun. 11, 2021.
(Continued)

*Primary Examiner* — Tremesha S Willis
(74) *Attorney, Agent, or Firm* — Birch, Stewart, Kolasch & Birch, LLP

(57) ABSTRACT

A circuit board for a non-combustion flavor inhaler includes a substrate and an electrically conductive ink pattern printed on the substrate. The substrate includes paper. A percentage weight loss of the paper from room temperature to 290° C. is less than 20% of a percentage weight loss of the paper from room temperature to 900° C. under a condition that allows air to flow at a flow rate of 100 mL/min while elevating a temperature of the air at a speed of 10° C./min.

18 Claims, 4 Drawing Sheets

(51) Int. Cl.
*A24F 40/57* (2020.01)
*H05K 1/02* (2006.01)
*H05K 1/03* (2006.01)
*H05K 1/09* (2006.01)
*H05K 3/12* (2006.01)
*A24F 40/50* (2020.01)
*B82Y 30/00* (2011.01)
*A24F 40/10* (2020.01)
*A24F 40/20* (2020.01)

(56) References Cited

U.S. PATENT DOCUMENTS

| | | |
|---|---|---|
| 2011/0226236 A1 | 9/2011 | Buchberger |
| 2014/0060554 A1 | 3/2014 | Collett et al. |
| 2017/0027063 A1* | 1/2017 | Schroder ............... C23C 18/31 |
| 2017/0119051 A1 | 5/2017 | Blandino et al. |

FOREIGN PATENT DOCUMENTS

| | | |
|---|---|---|
| JP | 3566721 B2 | 9/2004 |
| JP | 2016-190071 A | 11/2016 |
| WO | WO 94/06313 A1 | 3/1994 |
| WO | WO 2011/050964 A1 | 5/2011 |
| WO | WO 2015/035510 A1 | 3/2015 |
| WO | WO 2016/007516 A1 | 1/2016 |
| WO | WO 2016/166661 A1 | 10/2016 |
| WO | WO 2017/005471 A1 | 1/2017 |

OTHER PUBLICATIONS

Taiwanese Office Action and Search Report for Taiwanese Application No. 106140515, dated Apr. 19, 2021 with English translation.
International Search Report for PCT/JP2017/040809 (PCT/ISA/210) dated Feb. 13, 2018.
Korean Office Action for Korean Application No. 10-2020-7016041, dated Jan. 24, 2022, with English translation.

* cited by examiner

CIRCUIT BOARD FOR NON-COMBUSTION TYPE FLAVOR INHALER AND NON-COMBUSTION TYPE FLAVOR INHALER

CROSS REFERENCE TO RELATED APPLICATIONS

The present application is a continuation application of International Application No. PCT/JP2017/040809, filed on Nov. 13, 2017.

TECHNICAL FIELD

The present invention relates to a non-combustion flavor inhaler for savoring flavor components without combustion and a circuit board for the non-combustion flavor inhaler.

BACKGROUND ART

In place of cigarettes, there have been proposed non-combustion flavor inhalers like electronic cigarettes for savoring inhalation components that are generated through vaporization or atomization by heaters of aerosol sources and/or flavor sources, such as tobacco (Patent Literature (PTL) 1 to 7 below). Such a non-combustion flavor inhaler includes a heater for vaporizing or atomizing flavor sources and/or aerosol sources, a power supply for the heater, and a control circuit for the heater and the power supply.

The heaters described in PTL 1 to 5 include a circuit board that includes an electric conductor printed on an electrically insulating substrate. According to PTL 1, the electrically insulating substrate may include an electrically insulating material, such as ceramic like mica, glass, or paper.

CITATION LIST

Patent Literature

PTL 1: WO 2011/050964
PTL 2: US Patent Application Publication No. 2014/0060554
PTL 3: WO 2016/166661
PTL 4: WO 2016/007516
PTL 5: WO 2017/005471
PTL 6: WO 2015/035510
PTL 7: Japanese Unexamined Patent Application Publication No. 2016-190071

SUMMARY OF INVENTION

The first feature is summarized as a circuit board for a non-combustion flavor inhaler, including a substrate and an electrically conductive ink pattern printed on the substrate, wherein the substrate includes paper, and wherein a percentage weight loss of the paper from room temperature to 290° C. is less than 20% of a percentage weight loss of the paper from room temperature to 900° C. under a condition that allows air to flow at a flow rate of 100 mL/min while elevating a temperature of the air at a speed of 10° C./min.

The second feature is summarized as the circuit board of the first feature, wherein a surface of the paper is smoothed on a side on which the electrically conductive ink pattern is to be printed.

The third feature is summarized as the circuit board of the first or the second feature, wherein a surface on which the electrically conductive ink pattern is to be printed has a Bekk smoothness of 1.6 seconds or more.

The fourth feature is summarized as the circuit board of any one of the first to the third features, wherein the electrically conductive ink pattern is formed on an intermediate layer that the paper has on a surface.

The fifth feature is summarized as the circuit board of the fourth feature, wherein the intermediate layer is formed as a layer containing at least cellulose nanofibers.

The sixth feature is summarized as the circuit board of the fifth feature, wherein the intermediate layer further contains at least one of silica and calcium carbonate.

The seventh feature is summarized as the circuit board of any of the fourth to the sixth features, wherein the intermediate layer has a plurality of pores.

The eighth feature is summarized as the circuit board of any one of the first to the seventh features, wherein the circuit board includes a heater circuit.

The ninth feature is summarized as the circuit board of any one of the first to the eighth features, wherein the electrically conductive ink pattern is formed to be electrically disconnected at a temperature of 400° C. or higher.

The tenth feature is summarized as the circuit board of the ninth feature, wherein the electrically conductive ink pattern is formed to be disconnected at a temperature lower than a temperature at which a percentage weight loss of the paper reaches 90% of the percentage weight loss from room temperature to 900° C. under the condition.

The eleventh feature is summarized as the circuit board of any one of the first to the tenth features, further including a coating layer formed on a surface of the electrically conductive ink pattern, wherein the coating layer contains a material having a melting point or sol-gel transition temperature of 290° C. or lower and a flavor added into the material.

The twelfth feature is summarized as the circuit board of any one of the first to the eleventh features, wherein the substrate has an absorption rate of glycerol of more than 1%.

The thirteenth feature is summarized as a circuit board for a non-combustion flavor inhaler that includes a liquid inhalation component source to be vaporized or atomized by application of energy, including a substrate and an electrically conductive ink pattern printed on the substrate, wherein the substrate includes paper, and wherein a percentage weight loss of the paper from room temperature to a boiling point of the inhalation component source is less than 20% of a percentage weight loss of the paper from room temperature to 900° C. under a condition that allows air to flow at a flow rate of 100 mL/min while elevating a temperature of the air at a speed of 10° C./min.

The fourteenth feature is summarized as the circuit board of the thirteenth feature, wherein the circuit board includes a heater circuit.

The fifteenth feature is summarized as the circuit board of the thirteenth or the fourteenth feature, wherein the electrically conductive ink pattern is formed to be disconnected at a temperature higher than the inhalation component source and at a temperature lower than a temperature at which a percentage weight loss of the paper reaches 90% of the percentage weight loss from room temperature to 900° C. under the condition.

The sixteenth feature is summarized as the circuit board of any one of the thirteenth to the fifteenth features, further including a coating layer formed on a surface of the electrically conductive ink pattern, wherein the coating layer contains a material having a melting point or sol-gel transition temperature equal to or lower than a boiling point of the inhalation component source and a flavor added into the material.

The seventeenth feature is summarized as the circuit board of any one of the thirteenth to the sixteenth features, wherein the substrate has more than 1% of absorption of the inhalation component source.

The eighteenth feature is summarized as the circuit board of any one of the first to the seventeenth features, wherein the electrically conductive ink pattern contains an electrically conductive material and a dielectric material.

The nineteenth feature is summarized as the circuit board of the eighteenth feature, wherein the electrically conductive material is selected from at least one of an electrically conductive metal, an electrically conductive ceramic, a carbon material, and an electrically conducting polymer, and wherein the dielectric material is selected from at least one of a ceramic, a natural polymer, a synthetic polymer, and a surfactant.

The twentieth feature is summarized as the circuit board of any one of the first to the nineteenth features, wherein an ink for forming the electrically conductive ink pattern has a viscosity within a range of 1 mPa·s to 300 Pa·s.

The twenty first feature is summarized as a non-combustion flavor inhaler including the circuit board of any one of the first to the twentieth features, and a liquid inhalation component source to be vaporized or atomized by application of energy.

The twenty second feature is summarized as the non-combustion flavor inhaler of the twenty first feature, wherein the circuit board includes a heater circuit configured to vaporize or atomize the inhalation component source.

The twenty third feature is summarized as the non-combustion flavor inhaler of the twenty first or the twenty second feature, wherein the substrate of the circuit board is disposed to absorb the inhalation component source during use.

DESCRIPTION OF EMBODIMENTS

Figure 1:
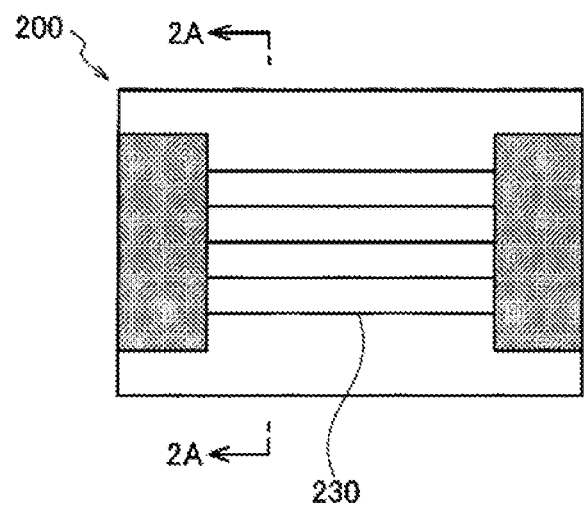
FIG. 1 is a schematic plan view of a circuit board for a flavor inhaler according to an embodiment.

Hereinafter, embodiments will be described. In the description of the drawings hereinafter, equivalent or similar signs are assigned to equivalent or similar parts. However, it should be noted that the drawings are schematic and each dimensional ratio and so forth differ from actual ones in some cases.

Accordingly, concrete dimensions and so forth should be judged by taking account of the following description. Moreover, it is natural that the respective dimensional relationships and/or ratios differ among drawings in some cases.

SUMMARY OF DISCLOSURE

Forming an electric circuit by printing an electrically conductive ink pattern on a substrate is under research and development. Exemplary common substrates include films and ceramics. In view of heat resistance, paper is not frequently used as a substrate.

According to an embodiment, a circuit board for a non-combustion flavor inhaler includes a substrate and an electrically conductive ink pattern printed on the substrate. The substrate includes paper. A percentage weight loss of the paper from room temperature to 290° C. is less than 20% of a percentage weight loss of the paper from room temperature to 900° C. under a condition that allows air to flow at a flow rate of 100 mL/min while elevating a temperature of the air at a speed of 10° C./min.

As a result, the weight of the paper constituting the substrate does not decrease much in a temperature range of room temperature to 290° C. When a liquid to be absorbed by the paper that constitutes the substrate primarily contains a compound that does not evaporate (vaporize) completely at a temperature of about 290° C. or lower, it is possible to ensure a state in which the liquid is sufficiently taken up by the paper. Here, common circuit boards of non-combustion flavor inhalers are typically used at a temperature of about 290° C. or lower. Accordingly, it is possible to ensure heat resistance as a circuit board for a non-combustion flavor inhaler by employing paper having the above-described characteristics as a substrate.

In particular, non-combustion flavor inhalers like electronic cigarettes include glycerol in many cases. Since glycerol is vaporized during use, the temperature is elevated to 290° C., which is the boiling point of glycerol. Even in this case, as long as the paper constituting a circuit board absorbs and retains a liquid, in other words, glycerol, the temperature of the paper is maintained at 290° C. or lower. Accordingly, by employing paper having the above-described characteristics as a substrate, it is possible to ensure heat resistance as a circuit board for a non-combustion flavor inhaler that includes glycerol, in particular.

According to another embodiment, a circuit board for a non-combustion flavor inhaler that includes a liquid inhalation component source to be vaporized or atomized by application of energy, includes a substrate and an electrically conductive ink pattern printed on the substrate. The substrate includes paper. A percentage weight loss of the paper from room temperature to a boiling point of the inhalation component source is less than 20% of a percentage weight loss of the paper from room temperature to 900° C. under a condition that allows air to flow at a flow rate of 100 mL/min while elevating a temperature of the air at a speed of 10° C./min.

As a result, the weight of the paper constituting the substrate does not decrease much in a temperature range of room temperature to the boiling point of the inhalation component source. In other words, the paper is in a state of sufficiently taking up the liquid inhalation component source in the temperature range of room temperature to the boiling point of the inhalation component source. For this reason, as long as the paper constituting the circuit board absorbs and retains the liquid inhalation component source, the temperature of the paper is maintained at a temperature of the boiling point or lower. Accordingly, it is possible to ensure heat resistance as a circuit board for a non-combustion flavor inhaler by employing paper having the above-described characteristics as a substrate.

First Embodiment (Circuit Board for Non-Combustion Flavor Inhalator)

Figure 2:
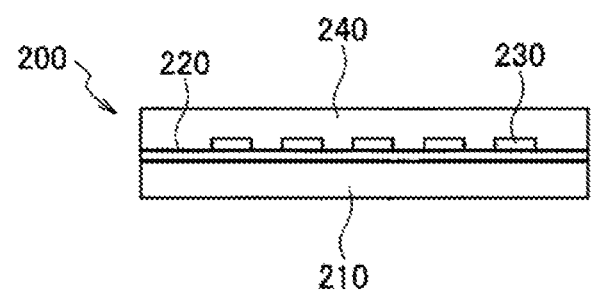
FIG. 2 is a schematic cross-sectional view of the circuit board according to an embodiment.

FIG. 1 is a schematic plan view of a circuit board for a flavor inhaler according to an embodiment. FIG. 2 is a schematic cross-sectional view of the circuit board according to an embodiment.

As described hereinafter, a flavor inhaler may be a non-combustion flavor inhaler for inhaling inhalation components (smoking flavor components) without involving combustion. Such a flavor inhaler may include a liquid inhalation component source to be vaporized or atomized by application of energy. The inhalation component source is vaporized or atomized, for example, through application of thermal energy by a heater. The vaporized or atomized inhalation component is inhaled by a user.

The inhalation component source is not particularly limited but may contain glycerol, for example. Alternatively, the inhalation component source may contain a mixture of glycerol and water, for example. Here, glycerol has a boiling point of about 290° C. and a liquid viscosity at 20° C. of 1,410 mPa·s. As just described, the inhalation component source typically vaporizes in the range of 100° C. to 290° C. Moreover, in the temperature range of 100° C. to 290° C., the liquid viscosity of the inhalation component source is 1,410 mPa·s or lower. The circuit board of the embodiment described hereinafter is particularly suitable for a flavor inhaler that uses such an inhalation component source.

A circuit board 200 includes a substrate 210 and an electrically conductive ink pattern 230 printed on the substrate 210. The electrically conductive ink pattern 230 is a pattern that constitutes an electric circuit. The circuit board 200 may be used as a control circuit for controlling the operation of a flavor inhaler or used as a heater circuit for applying thermal energy to an inhalation component source.

The electrically conductive ink pattern 230 is formed from an electrically conductive paste containing at least an electrically conductive material. The electrically conductive material is selected from at least one of an electrically conductive metal, an electrically conductive ceramic, a carbon material, and an electrically conducting polymer. Such electrically conductive metals may include at least one material selected from Ag, Al, Ni, Pt, Au, Cu, and W, for example. Such carbon materials may include at least one material selected from graphene, carbon nanotubes, graphite, activated carbon, acetylene black, and Ketjen black, for example. Such electrically conducting polymers may include at least one material selected from polythiophene, poly(styrenesulfonic acid), an oligo(thiophene), polypyrrole, and polyaniline, for example. The electrically conductive ink pattern 230 may be formed on the substrate 210 by screen printing, screen offset printing, ink-jet printing, flexographic printing, gravure printing, or offset printing, for example. The ink viscosity at room temperature is preferably within the range of 1 mPa·s to 300 Pa·s. In particular, screen printing or screen offset printing is preferable due to thick ink patterns. In this case, the viscosity at room temperature is preferably within the range of 1 Pa·s to 300 Pa·s, which is suitable for screen printing.

The electrically conductive ink pattern 230 may further contain, as necessary, a dielectric material. The dielectric material is preferably selected from ceramics, natural polymers, synthetic polymers, or surfactants. The ceramics may include at least one material selected from barium titanate, calcium carbonate, silica, aluminum oxide, magnesium oxide, and calcium oxide, for example. The natural polymers may include at least one material selected from a cellulose derivative, a polysaccharide, an acrylic polymer, a glycol-based polymer, pectin, chitosan, and chitin, for example.

The dielectric material contained in the electrically conductive ink pattern 230 may be barium titanate, for example. In this case, the amount of the dielectric material added is preferably within the range of 10 to 50% by weight based on the total electrically conductive ink pattern 230. Further, the electrically conductive ink pattern 230 may contain a small amount of diluent, such as toluene. The addition ratio of toluene based on the total electrically conductive paste is within the range of preferably 0 to 5% by weight and more preferably 0 to 10% by weight.

By incorporating a dielectric material into the electrically conductive ink pattern 230, it is possible to increase the electric resistance of the electrically conductive ink pattern 230. As a result, the circuit board 200 can be suitably used as a heater circuit. In particular, in view of application of the circuit board 200 to small handheld non-combustion flavor inhalers, it is necessary to realize a relatively high electric resistance by a small heater circuit. As described above, by incorporating a dielectric material into the electrically conductive ink pattern 230, it is possible to increase the electric resistance of the electrically conductive ink pattern and to increase the amount of heat generation even by a small heater circuit.

In view of application of a heater circuit to a non-combustion flavor inhaler, the electric resistance of the heater circuit is preferably 0.01 to 10Ω and more preferably 0.1 to 1Ω.

When heater circuits have the same electric resistance and the same current flows the respective electrically conductive ink patterns, an electrically conductive ink pattern formed as a narrower pattern and formed from a material having a higher electric resistance can increase the amount of heat generation per unit power and thus facilitates efficient vaporization or atomization for aerosol generation. Moreover, since the electrically conductive ink pattern can be thickened by controlling the electric resistance, it is possible to prevent disconnection due to overcurrent, which is a concern involved in vaporization and atomization for aerosol generation.

The electrically conductive ink pattern may have any shape provided that the shape has continuity. However, to avoid wiring disconnection when the circuit board 200 is folded or bent, a shape that can disperse stress applied to the electrically conductive ink pattern, for example, a curved line shape, such as a wavy line or a spiral, is preferable.

The substrate 210 that constitutes the circuit board 200 includes paper. The paper is not particularly limited but may be made of filter paper or glassine, for example. Since the substrate 210 includes paper, it is possible to form a light-weight thin circuit board 200. Moreover, since the circuit board 200 can be rolled or bent, it is also possible to easily mount the circuit board 200, for example, inside a small handheld flavor inhaler.

In the embodiment, the electrically conductive ink pattern 230 is formed on an intermediate layer 220 provided on the surface of the paper. The "intermediate layer" herein means a layer existing between a layer made of a proper paper raw material and the electrically conductive ink pattern 230. Part of the intermediate layer 220 may be exposed outside in portions where the electrically conductive ink pattern 230 is absent.

The intermediate layer 220 is preferably formed as a layer containing at least one of silica, calcium carbonate, and cellulose nanofibers, for example. More preferably, the intermediate layer 220 is formed as a layer containing silica, calcium carbonate, and cellulose nanofibers.

Alternatively to the above-mentioned example, the intermediate layer 220 may be formed from a material, such as a plastic film, rubber, or glass, attached to the surface of the paper as the substrate 210. In this case, the intermediate layer 220 may have a plurality of pores. Preferably, the pore size is $3.0 \times 10^4$ μm² or more and $1.0 \times 10^5$ μm² or less, and the porosity is within the range of 10% to 50%.

The circuit board 200 may include, as necessary, a coating layer 240 that covers the electrically conductive ink pattern 230. The coating layer 240 may contain a thermoresponsive material having a melting point or sol-gel transition temperature equal to or lower than the boiling point of an inhalation component source, for example, 70° C. or higher and 290° C. or lower; and a flavor added into the thermoresponsive material. The thermoresponsive material may be a wax having a melting point of 70° C. to 100° C., for example. The flavor is not particularly limited, but citral may be used, for example.

The thermoresponsive material melts upon heating and releases the flavor into the atmosphere. Accordingly, it is possible to allow a user to sense the flavor by releasing the flavor into the atmosphere during use of the circuit board, for example, a heater circuit. In particular, when the melting point or sol-gel transition temperature of the thermoresponsive material is equal to or lower than the boiling point of an inhalation component source, it is possible to release the flavor from the thermoresponsive material before atomization or vaporization of the inhalation component source.

The coating layer 240 may further include another coating material that covers the above-described thermoresponsive material. Such a coating material is preferably formed from a material having a melting point or sol-gel transition temperature lower than the melting point or sol-gel transition temperature of the thermoresponsive material. The coating material may be a wax having a melting point of 60° C. to 70° C., for example. By covering the thermoresponsive material containing the flavor with such a coating material, it is possible to suppress volatilization of the flavor into the atmosphere during non-use of the circuit board 200.

(Characteristics of Substrate)

Figure 3:
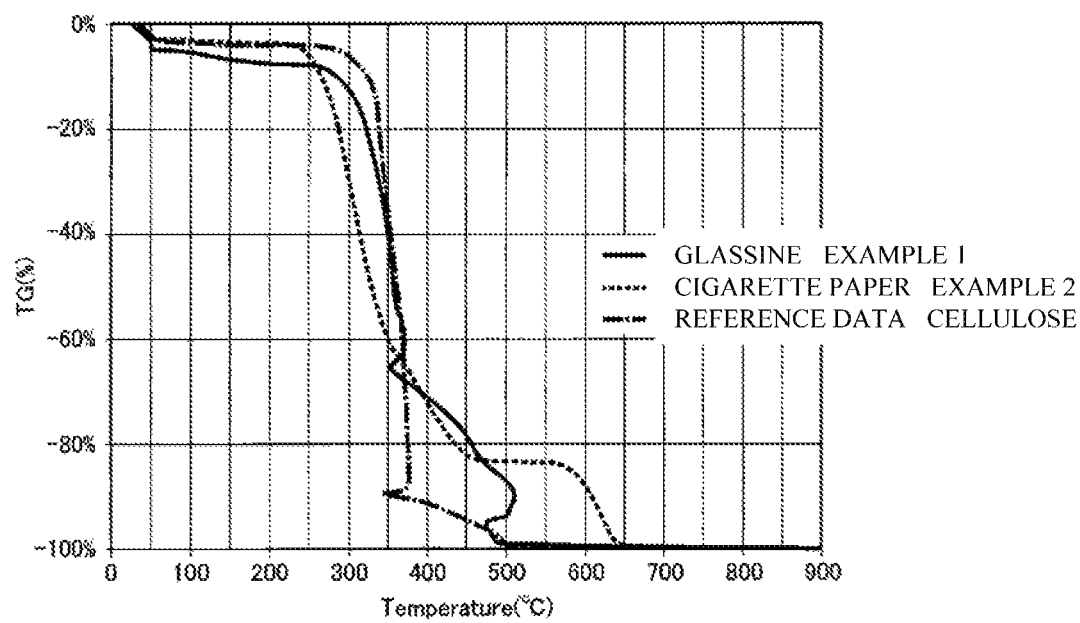
FIG. 3 is a graph showing the characteristics of substrates that constitute the circuit board.

The characteristics of the paper as the substrate 210 according to the embodiment will now be described. FIG. 3 shows thermogravimetric analysis results for the paper according to the Examples and for cellulose as a reference example. Thermogravimetric analysis can be performed by a thermogravimetric/thermal differential analyzer, for example.

The paper according to Example 1 is glassine substantially containing 100% cellulose. The paper according to Example 2 is cigarette paper containing 73% of cellulose. Thermogravimetric analysis was performed for these paper and cellulose under a condition that allows air to flow at a flow rate of 100 mL/min while elevating a temperature of the air at a speed of 10° C./min. More specifically, the temperature was first elevated from 25° C. to 50° C. at a rate of 10° C./min, maintained at 50° C. for 30 minutes, then elevated again to 900° C. at a rate of 10° C./min, and finally maintained at 900° C. for 1 min.

In the graph of FIG. 3, the horizontal axis represents temperature and the vertical axis represents change in weight (TG (%)) of a sample (paper or cellulose). The negative TG values indicate a reduction in sample weight. On the vertical axis of the graph, "0%" indicates no change in sample weight and "−100%" indicates a sample weight of 0.

As in the foregoing, the inhalation component source typically vaporizes within the range of 100° C. to 290° C. Accordingly, the circuit board 200 to be applied to a non-combustion flavor inhaler preferably exhibits sufficient heat resistance at least in the temperature range of 290° C. or lower.

In view of this, the paper that constitutes the substrate 210 is characterized in that a percentage weight loss of the paper from room temperature to 290° C. is less than 20%, preferably less than 18%, and more preferably less than 15% of a percentage weight loss of the paper from room temperature to 900° C. under a condition that allows air to flow at a flow rate of 100 mL/min while elevating a temperature of the air at a speed of 10° C./min.

More preferably, the paper that constitutes the substrate 210 is characterized in that a percentage weight loss of the paper from room temperature to a boiling point of the inhalation component source is less than 20%, preferably less than 18%, and more preferably less than 15% of a percentage weight loss of the paper from room temperature to 900° C. under a condition that allows air to flow at a flow rate of 100 mL/min while elevating a temperature of the air at a speed of 10° C./min.

Referring to the graph of FIG. 3, the paper (glassine) according to Example 1 has a percentage weight loss from room temperature to 290° C. of less than 15%. Accordingly, the paper according to Example 1 is suitably used as the substrate 210 that constitutes the circuit board 200 for a non-combustion flavor inhaler.

The paper according to Example 2 has a percentage weight loss from room temperature to about 280° C. of 20%. Accordingly, the paper according to Example 2 can be used as the substrate 210 that constitutes the circuit board 200 for a non-combustion flavor inhaler that includes an inhalation component source having a boiling point of 280° C. or lower.

Here, the thermogravimetric analysis result for cellulose itself reveals that the temperature at which cellulose starts to lose the weight is higher than the corresponding temperatures for the paper according to the Examples. Accordingly, it can be presumed that paper containing more cellulose is more suitable for the substrate 210 that constitutes the circuit board 200 for a non-combustion flavor inhaler. Preferably, the paper contains 50 to 100% by weight of cellulose.

The electrically conductive ink pattern 230 of the circuit board 200 is preferably formed to be disconnected at a temperature lower than a temperature at which a percentage weight loss of the substrate (paper) reaches 90% and preferably 80% of a percentage weight loss from room temperature to 900° C. under a condition that allows air to flow at a flow rate of 100 mL/min while elevating a temperature of the air at a speed of 10° C./min. As a result, the electrically conductive ink pattern is disconnected before the paper as the substrate 210 burns. Accordingly, it is possible to enhance the safety of the circuit board, in particular, a heater circuit.

The electrically conductive ink pattern 230 of the circuit board 200 may be formed to be electrically disconnected at a temperature of 400° C. or higher, for example.

(Liquid Absorption Characteristics of Substrate)

The circuit board 200 is preferably formed from paper that can absorb an inhalation component source, for example, glycerol. Specifically, the paper that constitutes the substrate 210 has an absorption rate of an inhalation component source, in particular, glycerol of preferably more than 1%, more preferably more than 10%, and further preferably more than 15%. As a result, the circuit board 200 can absorb and retain the inhalation component source within a flavor inhaler. For this reason, heat resistance of the circuit board 200 is further enhanced.

Further, as described hereinafter, the circuit board 200 can be used as a heater circuit that absorbs an inhalation component source while vaporizing or atomizing the absorbed inhalation component source. In this case, the circuit board 200 can be suitably used as a heater circuit that absorbs an inhalation component source while vaporizing or atomizing the absorbed inhalation component source.

Table 1 below shows substrate component materials and the absorption rate of glycerol. Table 1 reveals that when the circuit board 200 is used as a heater circuit that vaporizes or atomizes absorbed glycerol, paper is preferable, as the substrate 210, to a plastic film like a polypropylene film.

TABLE 1

| | Substrate component material | Glycerol absorption rate [%] |
|---|---|---|
| Reference Ex. | Polypropylene film | 1 |
| Ex. 1 | Glassine (100% cellulose, surface-uncoated) | 18.6 |
| Ex. 2 | Filter paper (100% cellulose, surface-uncoated) | 47.1 |
| Ex. 3 | Filter paper + coating (0.5% cellulose nanofiber) | 46.2 |
| Ex. 4 | Filter paper + coating (1.0% cellulose nanofiber) | 53.3 |
| Ex. 5 | Filter paper + coating (0.5% cellulose nanofiber, 10% calcium carbonate) | 49.4 |
| Ex. 6 | Filter paper + coating (0.5% cellulose nanofiber, 30% calcium carbonate) | 20.4 |
| Ex. 7 | Filter paper + coating (1.0% cellulose nanofiber, 10% calcium carbonate) | 42.9 |
| Ex. 8 | Filter paper + coating (1.0% cellulose nanofiber, 30% calcium carbonate) | 57.8 |

As shown in Table 1, paper has a higher absorption rate of glycerol than a plastic film like a polypropylene film. Moreover, a high absorption rate of glycerol can be maintained even in Examples 3 to 8 in which filter paper is surface-coated with cellulose nanofibers and/or calcium carbonate. Accordingly, Examples 3 to 8 can advantageously maintain high absorption rate of glycerol as well as surface smoothness of the substrate due to the coatings.

The liquid absorption by a sample (substrate) herein is evaluated as follows. First, a prepared sample (5 cm×5 cm piece of paper) was supplied with drops of 40 mg of glycerol by a micropipette and left to stand for 30 seconds. Subsequently, a filter paper (Whatman Filter Paper No. 2) was placed on the sample, a 200 g-weight was placed on the filter paper, and the sample was left to stand for 10 seconds. After that, unabsorbed glycerol by the sample was absorbed by another filter paper. This procedure was repeated twice.

Next, an absorption rate was determined by calculating the amount of absorbed glycerol from a change between a sample weight measured in advance and a sample weight after the above-described procedure.

(Smoothness)

A surface of the paper constituting the substrate 210 is preferably smoothed on a side on which the electrically conductive ink pattern 230 is to be printed. The surface of the paper constituting the substrate 210 on a side on which the electrically conductive ink pattern 230 is to be printed, in other words, the surface of the paper itself or the surface of the intermediate layer 220 has a Bekk smoothness of preferably 1.6 seconds or more and more preferably 3.0 seconds or more.

Table 2 below shows materials of paper that constitutes the substrate 210, Bekk smoothness of the paper, and printability of an electrically conductive ink pattern. As shown below, the present inventors found that the electrically conductive ink pattern 230 can be printed highly accurately by enhancing a Bekk smoothness even when the substrate 210 includes paper. In particular, it was found that the printability of an electrically conductive ink pattern is enhanced by surface coating of filter paper with cellulose nanofibers.

Moreover, it was found that even when the electrically conductive ink pattern 230 includes calcium carbonate (ink receiving layer), a sufficiently high Bekk smoothness of the surface of the intermediate layer 220 can be maintained by addition of cellulose nanofibers to the coatings.

TABLE 2

| | Substrate component material | Smoothness [sec] | Printability |
|---|---|---|---|
| Reference Ex. | Filter paper | 1.6 | Δ |
| Ex. 1 | Glassine | 17.1 | ○ |
| Ex. 3 | Filter paper + coating (0.5% cellulose nanofiber) | 3.0 | ○ |
| Ex. 4 | Filter paper + coating (1.0% cellulose nanofiber) | 3.2 | ○ |
| Ex. 5 | Filter paper + coating (0.5% cellulose nanofiber, 10% calcium carbonate) | 2.0 | ○ |
| Ex. 7 | Filter paper + coating (1.0% cellulose nanofiber, 10% calcium carbonate) | 1.8 | ○ |
| Ex. 8 | Filter paper + coating (1.0% cellulose nanofiber, 30% calcium carbonate) | 4.5 | ○ |

Here, printability was determined on the basis of variations in electric resistance of an electrically conductive ink pattern when a specific circuit pattern was printed a plurality of times. A small variation in electric resistance, specifically a variation coefficient of 10% or less was evaluated as "○". A moderately large variation in electric resistance, specifically, a variation coefficient of 10% to 20% was evaluated as "Δ." Here, the variation coefficient is defined as a value of standard deviation divided by mean.

Herein, the Bekk smoothness is determined by a measurement method in accordance with JIS P 8119. For example, the Bekk smoothness is measured by a Bekk smoothness tester (from Toyo Seiki Seisaku-sho, Ltd.).

Specifically, first, a specimen of a predetermined dimension is taken from paper that constitutes a substrate of a circuit board. A measurement surface of the specimen is placed facing a glass surface of a Bekk smoothness tester, a rubber pad-attached platen is placed on the specimen, and a mercury column is then raised slightly above the marking at 380 mm (50.7 kPa).

Next, a stopwatch is started when the mercury column falls to the marking at 380 mm (50.7 kPa), and the time for the mercury column to reach 360 mm (48.0 kPa) is measured in seconds. The measured time represents a Bekk smoothness. When the time for 10 mL air to pass through takes 300 seconds or more, the time for 1 mL air to pass through is accurately measured and the time multiplied by 10 may be regarded as a Bekk smoothness.

Herein, the above-described measurement was repeated three times for each specimen while obtaining smoothness three times. An average of the obtained three smoothness values was defined as "smoothness" in the present specification.

(Composition of Electrically Conductive Ink)

Figure 4:
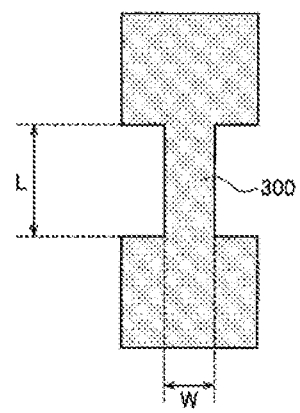
FIG. 4 illustrates an electrically conductive ink pattern employed for an experiment on printability.

A printing pattern as illustrated in FIG. 4 was prepared with a 350 mesh nylon and printed on glassine (substrate) by a screen printing machine (WHT Labo from Mino Group Co., Ltd.). Barium titanate was added to a predetermined amount of silver paste (from Mino Group Co., Ltd.), and 4% toluene was further added for uniform mixing through stirring and degassing. Before measuring electric resistance, it was confirmed that a battery lead and a heater are in contact under a force of 10 N or higher and that the same electric resistance is obtained as for the case in which a battery lead and a heater are soldered. Here, the electrically conductive ink pattern has a narrow straight line portion 300 in length L of 10 mm and width of 2 mm.

By incorporating barium titanate as a dielectric material into the electrically conductive ink pattern, the electric resistance increased as shown in the following Table. The resistance value increased in proportion to a decrease in ratio of the electrically conductive material due to addition of barium titanate. From these results, it was found that the electric resistance of an electrically conductive ink pattern can be controlled by addition of a dielectric material like barium titanate.

TABLE 3

| Ratio of $BaTiO_3$ added [%] | Ratio of toluene added [%] | Resistance value [Ω] |
|---|---|---|
| 0% | 4 | 0.48 |
| 10% | 4 | 0.59 |
| 30% | 4 | 0.82 |
| 50% | 4 | 0.96 |

(Flavor Inhaler)

Figure 5:
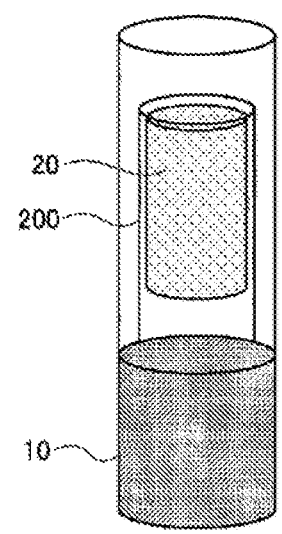
FIG. 5 illustrates an exemplary flavor inhaler.

Hereinafter, a flavor inhaler according to an embodiment will be described. FIG. 5 is a schematic view illustrating an exemplary flavor inhaler. The flavor inhaler may be a non-combustion flavor inhaler for inhaling an inhalation component (smoking flavor component) without involving combustion.

A flavor inhaler 100 may include a power supply 10, a circuit board 200, and a liquid aerosol source 20 to be vaporized or atomized by application of energy. The power supply 40 may be a rechargeable battery like a lithium-ion secondary battery, for example.

The circuit board 200 may be the above-described one and may include a heater circuit configured to vaporize or atomize an inhalation component source 20. The power supply 10 is electrically connected to the circuit board 200 and supplies power to the circuit board 200. In the circuit board 200, the heater circuit generates heat upon supply of power.

The aerosol source 20 may be a liquid at normal temperature. As the aerosol source, for example, a polyhydric alcohol, such as glycerol, may be used. The aerosol source 20 may contain a flavor component. Alternatively, the aerosol source may contain a tobacco raw material or an extract derived from a tobacco raw material that releases a smoking flavor component upon heating.

The aerosol source 20 may be retained, for example, by a porous body formed from a material, such as a resin web. In a preferable embodiment, a substrate 210 of the circuit board 200 is in contact with the porous body. The aerosol source 20 retained by the porous body is absorbed by paper that constitutes the substrate 210 of the circuit board 200.

The circuit board 200 generates heat, thereby vaporizing or atomizing the aerosol source absorbed by the substrate 210. The vaporized or atomized aerosol source is inhaled by a user.

In the flavor inhaler of the above-described embodiment, the substrate 210 of the circuit board 200 preferably has the above-mentioned pores. As a result, the substrate 210 can absorb and retain more aerosol source, thereby facilitating vaporization or atomization of the aerosol source.

Figure 6:
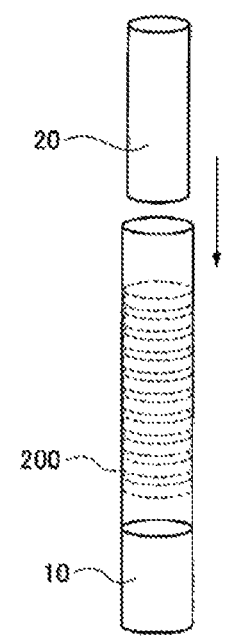
FIG. 6 illustrates another exemplary flavor inhaler.

The configuration of a non-combustion flavor inhaler is not limited to the above-described one. For example, FIG. 6 is a schematic view illustrating an exemplary flavor inhaler having another configuration. The flavor inhaler illustrated in FIG. 6 includes an aerosol source 20 formed as a solid and a cylindrical section that surrounds the aerosol source 20. The aerosol source 20 formed as a solid may contain, for example, a polyhydric alcohol like glycerol.

The above-described circuit board 200 may be wound around the cylindrical section that surrounds the aerosol source 20. Alternatively, the cylindrical section per se may be formed from a cylindrically rolled circuit board 200.

Even in this case, the aerosol source 20 can be vaporized or atomized through heating by a heater circuit included in the circuit board 200.

The present invention is described by means of the foregoing embodiments. However, it should not be understood that the description and the drawings as part of this disclosure limit the present invention. From this disclosure, various alternative embodiments, working examples, and operational techniques would become obvious to those skilled in the art.

In the foregoing embodiments, for example, the circuit board 200 including a heater circuit is described in particular detail. However, the circuit board 200 is also applicable to circuit boards without a heater circuit, for example, to those having a control circuit for controlling the operation of a flavor inhaler.

The invention claimed is:

1. A non-combustion flavor inhaler, comprising:
   a circuit board comprising a substrate and an electrically conductive ink pattern printed on the substrate; and
   a liquid inhalation component source to be vaporized or atomized by application of energy;
   wherein the substrate comprises paper,
   wherein a percentage weight loss of the paper from room temperature to 290° C. is less than 20% of a percentage weight loss of the paper from room temperature to 900° C. under a condition that allows air to flow at a flow rate of 100 mL/min while elevating a temperature of the air at a speed of 10° C./min,
   wherein the liquid inhalation component source is an aerosol source containing a tobacco raw material or an extract derived from a tobacco raw material,
   wherein the circuit board further comprises a heater circuit configured to vaporize or atomize the inhalation component source, and
   wherein the substrate of the circuit board is configured to absorb the inhalation component source during use.

2. The non-combustion flavor inhaler according to claim 1, wherein a surface of the paper is smoothed on a side on which the electrically conductive ink pattern is to be printed.

3. The non-combustion flavor inhaler according to claim 1, wherein a surface on which the electrically conductive ink pattern is to be printed has a Bekk smoothness of 1.6 seconds or more.

4. The non-combustion flavor inhaler according to claim 1, wherein the electrically conductive ink pattern is formed on an intermediate layer that the paper has on a surface.

5. The non-combustion flavor inhaler according to claim 4, wherein the intermediate layer is formed as a layer comprising at least cellulose nanofibers.

6. The non-combustion flavor inhaler according to claim 5, wherein the intermediate layer further comprises at least one of silica and calcium carbonate.

7. The non-combustion flavor inhaler according to claim 4, wherein the intermediate layer has a plurality of pores.

8. The non-combustion flavor inhaler according to claim 1, wherein the electrically conductive ink pattern is formed to be electrically disconnected at a temperature of 400° C. or higher.

9. The non-combustion flavor inhaler according to claim 8, wherein the electrically conductive ink pattern is formed to be disconnected at a temperature lower than a temperature at which a percentage weight loss of the paper reaches 90% of the percentage weight loss from room temperature to 900° C. under the condition.

10. The non-combustion flavor inhaler according to claim 1, further comprising a coating layer formed on a surface of the electrically conductive ink pattern,
wherein the coating layer comprises a material having a melting point or sol-gel transition temperature of 290° C. or lower and a flavor added into the material.

11. The non-combustion flavor inhaler according to claim 1, wherein the substrate has an absorption rate of glycerol of more than 1%.

12. A non-combustion flavor inhaler that comprises a liquid inhalation component source to be vaporized or atomized by application of energy, comprising:
a circuit board comprising a substrate and an electrically conductive ink pattern printed on the substrate; and
a liquid inhalation component source to be vaporized or atomized by application of energy;
wherein the substrate comprises paper,
wherein a percentage weight loss of the paper from room temperature to a boiling point of the inhalation component source is less than 20% of a percentage weight loss of the paper from room temperature to 900° C. under a condition that allows air to flow at a flow rate of 100 mL/min while elevating a temperature of the air at a speed of 10° C./min,
wherein the liquid inhalation component source is an aerosol source containing a tobacco raw material or an extract derived from a tobacco raw material,
wherein the circuit board further comprises a heater circuit configured to vaporize or atomize the inhalation component source, and
wherein the substrate of the circuit board is configured to absorb the inhalation component source during use.

13. The non-combustion flavor inhaler according to claim 12, wherein the electrically conductive ink pattern is formed to be disconnected at a temperature higher than the inhalation component source and at a temperature lower than a temperature at which a percentage weight loss of the paper reaches 90% of the percentage weight loss from room temperature to 900° C. under the condition.

14. The non-combustion flavor inhaler according to claim 12, further comprising a coating layer formed on a surface of the electrically conductive ink pattern,
wherein the coating layer comprises a material having a melting point or sol-gel transition temperature equal to or lower than a boiling point of the inhalation component source and a flavor added into the material.

15. The non-combustion flavor inhaler according to claim 12, wherein the substrate has more than 1% of absorption of the inhalation component source.

16. The non-combustion flavor inhaler according to claim 1, wherein the electrically conductive ink pattern comprises an electrically conductive material and a dielectric material.

17. The non-combustion flavor inhaler according to claim 16, wherein the electrically conductive material is selected from at least one of an electrically conductive metal, an electrically conductive ceramic, a carbon material, and an electrically conducting polymer, and
wherein the dielectric material is selected from at least one of a ceramic, a natural polymer, a synthetic polymer, and a surfactant.

18. The non-combustion flavor inhaler according to claim 1, wherein an ink for forming the electrically conductive ink pattern has a viscosity within a range of 1 mPa·s to 300 Pa·s.

* * * * *